United States Patent [19]
Sinfelt et al.

[11] 3,989,674
[45] Nov. 2, 1976

[54] NOVEL GOLD-COPPER CATALYSTS FOR THE PARTIAL OXIDATION OF OLEFINS

[75] Inventors: John H. Sinfelt, Berkeley Heights; Allan E. Barnett, Westfield, both of N.J.

[73] Assignee: Exxon Research and Engineering Company, Linden, N.J.

[22] Filed: Mar. 26, 1969

[21] Appl. No.: 810,846

[52] U.S. Cl. ............................................ 260/604 R
[51] Int. Cl.² .......................................... C07C 45/02
[58] Field of Search ......................... 260/604 R, 599

[56] References Cited
FOREIGN PATENTS OR APPLICATIONS
23,646  10/1965  Japan ................................. 260/604

Primary Examiner—James O. Thomas, Jr.
Assistant Examiner—W. B. Lone
Attorney, Agent, or Firm—Robert J. Baran

[57] ABSTRACT

In the partial oxidation of olefinic hydrocarbons directly to their corresponding unsaturated carbonyl compounds, a significant increase in selectivity to the unsaturated carbonyl compounds is obtained by reacting an olefinic compound with oxygen in the presence of a novel bimetallic catalyst system comprising a combination of gold and copper.

9 Claims, No Drawings

NOVEL GOLD-COPPER CATALYSTS FOR THE PARTIAL OXIDATION OF OLEFINS

BACKGROUND OF THE INVENTION

This invention relates to the catalytic partial oxidation of olefinic hydrocarbons directly to their corresponding unsaturated carbonyl compounds, e.g. aldehydes and ketones. More specifically, this invention relates to a process for improving the selectivity to unsaturated aldehydes and ketones by reacting olefinic hydrocarbons and a source of oxygen on a novel bimetallic catalyst system which is composed of a combination of gold and copper. Other partial oxidations for which this catalyst is useful include the oxidation of aromatics to their corresponding aldehydes, e.g., toluene to benzaldehyde and xylene to tolualdehyde. In a preferred embodiment of this invention, acrolein is selectively prepared by passing a mixture of propylene and a source of oxygen over a supported gold-copper bimetallic catalyst system.

DESCRIPTION OF THE PRIOR ART

Many attempts have been made to produce unsaturated aldehydes, such as acrolein, by catalytic dehydrogenation and by catalytic oxidation of unsaturated alcohols. The catalytic dehydrogenation and catalytic oxidation of unsaturated alcohols to unsaturated aldehydes have been shown to be commercially unacceptable to the industry due to the high production costs of carrying out these processes.

It has previously been shown that propylene can be oxidized to acrolein by passing a mixture of hydrocarbons and a source of oxygen over a silica gel-supported copper oxide catalyst at elevated temperatures (U.S. Pat. No. 2,627,527). While the copper-silica catalysts have for some time been the preferred catalysts for the oxidation of olefinic hydrocarbons to unsaturated aldehydes, it has now been discovered that significantly greater selectivity to the unsaturated aldehyde can be obtained by utilizing the novel catalyst system herein described.

SUMMARY OF THE INVENTION

In accordance with the instant invention, high selectivities to unsaturated aldehydes or ketones are obtained by the reaction of an olefinic compound with a source of oxygen, at elevated temperatures, in the presence of a novel bimetallic copper-gold catalyst.

The catalyst system may be prepared by impregnating a supporting material such as silica gel with an aqueous solution of a salt of copper (e.g., copper nitrate) and gold (e.g., auric chloride). The catalysts are then dried, reduced in flowing hydrogen and finally calcined in air at elevated temperatures.

While not wishing to be bound to any particular theory, the novel bimetallic copper-gold catalyst, after reduction in hydrogen at elevated temperature, appears to consist of a copper-gold alloy. Here the term alloy includes bulk alloy formation as well as where alloy formation may be limited to a surface layer or region (i.e., surface alloys). While catalysis is actually taking place, however, the state of the catalyst may be different from what it is after reduction in hydrogen. During the catalysis, the catalyst is probably oxidized to a degree, at least in the surface layer. Thus, the copper in the surface layer may well be present as the cuprous ion. It appears that one may have gold and cuprous oxide interspersed in the surface during catalytic oxidation.

The gold-copper bimetallic catalyst system of the instant invention may either be unsupported or supported on an inert substrate material. Representative, nonlimiting examples of such inert substrate materials, which can be impregnated with a solution containing the copper and gold metals, may be generally classified as refractory oxides and include, but are not limited to: silica, alumina, magnesia, thoria, zirconia, and combinations thereof. Other support materials such as kieselguhr, asbestos, pumice and silicon carbide may also be used.

DESCRIPTION OF THE PREFERRED EMBODIMENT

In a preferred embodiment of this invention, the catalyst system of the instant invention is employed to partially oxidize olefinic hydrocarbons directly to their corresponding (having the same number of carbon atoms as the starting olefinic compound) unsaturated carbonyl compounds. In a more preferred embodiment of this invention, olefinic compounds containing from 3 to about 18 carbon atoms and having the following general formula:

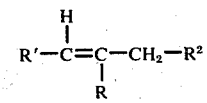

wherein R, R' and R² are each selected from the group consisting of hydrogen or a $C_1$ to $C_5$ alkyl group, may be partially oxidized over the catalyst system of the instant invention to their corresponding carbonyl compounds in high selectivities. It is to be understood that when $R^2$ is hydrogen, the olefinic compound will be partially oxidized to its corresponding unsaturated aldehyde in high selectivities. When $R^2$ is an alkyl radical, the olefinic compound will be oxidized, in accordance with the instant invention, to its corresponding unsaturated ketone. The most preferred starting olefinic compounds are propylene, isobutylene and 1-butene. Thus, propylene and isobutylene (where $R^2$ is hydrogen) are partially oxidized over the catalyst system of this invention to acrolein and methacrolein respectively, whereas 1-butene is partially oxidized to methyl vinyl ketone in high selectivities. In addition, diolefins such as isoprene, piperylene, and 2,4-hexadiene can likewise be oxidized in high selectivities to alpha vinyl acrolein, 2,4-pentadienal and 2,4-hexadienal respectively. Furthermore, methylated aromatics such as toluene and xylene can be oxidized in high selectivities to their corresponding aldehydes e.g. benzaldehyde and tolualdehyde respectively.

The amount of gold on the support material (refractory oxide) may range from about 0.1 to about 25 wt. %, based on the total catalyst and more preferably from about 0.5 to about 5.0 wt. %. The amount of the copper on the inert substrate material may likewise vary from about 0.1 to 50 wt. % based on the total catalyst and more preferably from about 0.5 to about 5.0 wt. %. In either its supported or unsupported form, the gold-copper molar ratio may vary from about 0.01 to 99., i.e. from about 1 part gold, 99 parts copper to about 99 parts gold, 1 part copper. More preferably, the molar ratio of gold to copper in the catalyst system of the instant invention may vary from about 0.25 to 4., i.e. from 1 part gold, 4 parts copper to 4 parts gold, 1 part copper. Most preferably, the gold-copper molar ratio is about 1.30 to 1.0, i.e. about 1.30 parts gold to about 1.0 part copper.

The above-described gold-copper catalyst combination is dried at a temperature in the range of from about 212° to 250° F. The dried catalyst is then reduced in flowing hydrogen at a temperature of about 400° to 900° F. for about 2 to 16 hours. Lastly, the reduced catalyst system is calcined in air at a temperature of about 600° to 1300° F. for about 2 to 16 hours.

The above-described olefinic compounds are passed in a mixture with a source of oxygen, e.g. air, over the catalyst system of the instant invention. The amount of oxygen employed may vary from as high as 10 moles of oxygen per mole of olefinic hydrocarbon to preferably 0.2 to 4 moles of oxygen per mole of olefinic hydrocarbon. Diluents other than nitrogen, such as steam, paraffinic hydrocarbons such as methane, ethane, propane and the like, may likewise be employed.

The reaction conditions under which the above-described process may be conducted may vary widely and primarily depend upon the particular olefin being oxidized. Generally, the reaction is conducted at a temperature in the range of from about 300° to 700° F. More preferably, temperatures of about 400° to 650° F. have been found to be preferred for the oxidation of olefins with a temperature in the range of about 475° to 600° F. being preferred for the oxidation of propylene to acrolein. Likewise, the oxidation process may be carried out over a wide range of pressures. Desirably, the reaction should be conducted at a pressure in the range of from about 0.5 to 10 atmospheres and more preferably from about 1 to 5 atmospheres. Either a fixed bed or fluidized bed may be employed. In view of the fact that the temperature must be accurately controlled to prevent excessive oxidation to water and carbon dioxide, a fluidized bed unit or a modification of the latter may be preferred because of the ease of controlling operating variables, particularly temperature.

The space velocity (volumes of vapor per volume of catalyst per hour) may vary from about 50 V/V/Hr. to about 5000 V/V/Hr. More preferably, the space velocity is in the range of from about 100 V/V/Hr. to about 1000 V/V/Hr.

Another distinct advantage of the catalyst system of the instant invention is that the catalyst need not be regenerated as with some partial oxidation catalysts.

This process is not dependent upon a particular method of recovery of the useful products of the oxidation. The unsaturated aldehyde or ketone product may be recovered by standard procedures involving condensation, fractionation and the like.

This invention will be further illustrated by the following examples. However, no limitations, other than those incorporated in the appended claims, are to be implied.

EXAMPLE 1

The partial oxidation of an olefin (propylene) to its corresponding unsaturated aldehyde (acrolein) was carried out over a copper-silica catalyst, a gold-silica catalyst, and the catalyst system of the instant invention comprising the bimetallic gold-copper combination on silica.

The copper-silica catalyst was prepared by impregnation of Davison 926 silica gel with a copper nitrate solution. The gold-silica catalyst was prepared by impregnation of Davison 926 silica gel with a solution of auric chloride. The gold-copper catalyst system of the instant invention was prepared by impregnating the Davison 926 silica gel with a solution containing copper nitrate and auric chloride. A solution containing 0.29 gm. $HAuCl_4 \cdot 3H_2O$ and 0.11 gm. $Cu(NO_3)_2 \cdot 3H_2O$ per milliliter was employed for impregnation. The volume of solution per gram of silica gel was 0.35 milliliter. The catalysts were dried at 230° F., reduced for 2 hours in flowing hydrogen at 600° F., and finally calcined in air for 15 hours at 1250° F. The gold-copper molar ratio of this catalyst was 1.29 to 1, i.e. 1.29 parts gold to 1.0 parts copper.

Propylene, oxygen and a helium diluent were mixed in the molar ratio of 1:2:8 and passed at atmospheric pressure over the three types of catalysts described above. A total vapor space velocity of 500 volumes of gas per volume of catalyst per hour was employed. The catalyst charge was 10 cubic centimeters.

As can be seen from the results shown in Table I, it is clear that the bimetallic copper-gold catalyst system of the instant invention significantly increases the selectivity to the unsaturated aldehyde (acrolein) while maintaining excellent conversion rates of the olefin feed (propylene).

TABLE I

COMPARISON OF GOLD, COPPER, AND GOLD-COPPER COMBINATION CATALYSTS FOR OXIDATION OF PROPYLENE TO ACROLEIN

Conditions: Total vapor space velocity = 500 V/H/V, pressure = 1 atm., $C_3H_6:O_2:He$ mole ratio = 1:2:8, catalyst charge = 10 cc.

| Catalyst* | Temperature, °F. | % Propylene Conversion | % Selectivity To Acrolein |
|---|---|---|---|
| 5 wt. % Au | 608 | 7.4 | 39.8 |
|  | 627 | 10.5 | 32.9 |
| 5 wt. % Cu | 498 | 6.0 | 64.1 |
|  | 520 | 10.0 | 61.2 |
|  | 544 | 15.1 | 54.9 |
|  | 570 | 20.6 | 52.3 |
|  | 597 | 29.8 | 49.4 |
|  | 626 | 36.0 | 50.0 |
| 4 wt. % Au, 1 wt. % Cu | 510 | 10.7 | 72.6 |
|  | 535 | 18.3 | 70.2 |
|  | 540 | 23.5 | 71.8 |
|  | 565 | 32.5 | 70.4 |
|  | 582 | 40.8 | 61.9 |

*Silica (Davison 926) was employed as the support in all cases.

EXAMPLE 2

A mixture of isobutylene, oxygen, and a helium diluent in a molar ratio of 1:2:8 to 2:1:8 is passed over the copper-silica and copper-gold-silica catalysts of Example 1 at atmospheric pressure and temperatures in the range of 450° to 600° F. A total vapor space velocity in the range of 200 to 1000 volumes of gas per hour per volume of catalyst is employed. The copper-gold catalyst is more selective than the copper catalyst for the production of methacrolein. At a conversion level of 25%, the copper catalyst gives 50 to 60% selectivity to the methacrolein compared to 70 to 75% for the copper-gold catalyst.

EXAMPLE 3

A mixture of 1-butene, oxygen, and a helium diluent in a molar ratio of 1:2:8 to 2:1:8 is passed over the copper-silica and copper-gold-silica catalysts of Example 1 at atmospheric pressure and temperatures in the range of 450° to 600° F. A total vapor space velocity of 200 to 1000 volumes of gas per hour per volume of catalyst is used. The selectivity of conversion of 1-butene to methyl vinyl ketone is significantly higher over the copper-gold catalyst, about 55 to 65% compared to 30 to 50% for the copper catalyst, at a conversion level of 35%.

EXAMPLE 4

A mixture of toluene, oxygen, and a helium diluent in a molar ratio of 1:2:8 to 2:1:8 is treated in the same method described in Examples 1 and 3, using the same ranges of conditions. The selectivity of conversion to benzaldehyde is significantly higher over the copper-gold catalyst, about 75 to 80% compared to 65 to 70% for the copper catalyst, at conversion levels in the range of 15 to 30%.

What is claimed is:

1. A process for the partial oxidation of an unsubstituted monoolefinic compound, comprising from 3 to 18 carbon atoms, to its corresponding unsaturated carbonyl compound which comprises passing said monoolefinic compound in admixture with oxygen at a temperature in the range of from about 300° to about 700° F. over a catalyst comprising gold and copper, said catalyst having a molar ratio of gold to copper of from about 0.25 to 4.

2. A process for the partial oxidation of a monoolefinic hydrocarbon to its corresponding unsaturated carbonyl compound which comprises passing an unsubstituted monoolefinic hydrocarbon having the formula:

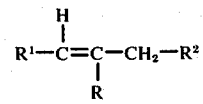

wherein R, $R^1$ and $R^2$ are each selected from the group consisting of hydrogen or a $C_1$ to $C_5$ alkyl group in admixture with oxygen over a catalyst consisting essentially of gold and copper, said catalyst having a molar ratio of gold to copper of from about 0.25 to about 4 at a temperature in the range of from about 300° to about 700° F.

3. The process for the partial oxidation of a monoolefinic hydrocarbon to its corresponding unsaturated aldehyde which comprises passing an unsubstituted monoolefinic hydrocarbon having the formula:

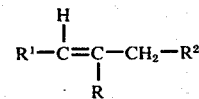

wherein $R^2$ is hydrogen and R and $R^1$ are each selected from the group consisting of $C_1$ to $C_5$ alkyl groups in admixture with oxygen over a catalyst consisting of a refractory oxide impregnated with gold and copper, said catalyst having a gold to copper molar ratio of from about 0.25 to about 4.

4. The process of claim 3 wherein the amount of gold on the refractory oxide is in the range of from about 0.1 to about 25 wt. %.

5. The process of claim 4 wherein the amount of copper on the refractory oxide is in the range of from about 0.1 to about 50 wt. %.

6. The process of claim 5 wherein the refractory oxide is silica.

7. The process of claim 6 wherein $R^1$ is hydrogen and $R^2$ is selected from the group consisting of hydrogen and a methyl group.

8. The process of claim 3 wherein said monoolefinic hydrocarbon is chosen from the group consisting of propylene, isobutylene and 1-butene.

9. The process for the partial oxidation of a methylated aromatic selected from the group consisting of toluene and xylene to its corresponding aldehyde which comprises passing said methylated aromatic in admixture with oxygen over a catalyst consisting of a refractory oxide impregnated with gold and copper, said catalyst having a gold-copper mole ratio of from about 0.25 to about 4.

* * * * *